United States Patent [19]

Weithmann et al.

[11] Patent Number: 5,547,970
[45] Date of Patent: Aug. 20, 1996

[54] USE OF LEFLUNOMIDE FOR INHIBITING TUMOR NECROSIS FACTOR ALPHA

[75] Inventors: Klaus U. Weithmann, Hofheim; Robert R. Bartlett, Darmstadt, both of Germany

[73] Assignee: Hoechst Aktiengesellschaft, Frankfurt am Main, Germany

[21] Appl. No.: 411,995

[22] Filed: Mar. 28, 1995

Related U.S. Application Data

[63] Continuation of Ser. No. 177,981, Jan. 6, 1994, abandoned.

[30] Foreign Application Priority Data

Jan. 8, 1993 [DE] Germany ............... 43 00 280.3

[51] Int. Cl.$^6$ .................................................. A61K 31/42
[52] U.S. Cl. ............................................................. 514/378
[58] Field of Search ............................................... 514/378

[56] References Cited

U.S. PATENT DOCUMENTS

| | | | |
|---|---|---|---|
| 4,351,841 | 9/1982 | Kammerer et al. | 514/378 |
| 4,965,276 | 10/1990 | Bartlett et al. | 514/378 |

FOREIGN PATENT DOCUMENTS

WO92/02822  2/1992  WIPO.

OTHER PUBLICATIONS

T. Mattar et al., "Effects of Leflunomide (HWA 486) on Mediators of . . . ", Immunobiology, 178(1–2):156 (1988).
T. Zielinski et al., "Effects of Leflunomide (HWA 486) on Cell Cycle . . . ", Immunobiology, 186(1–2):113 (1992).
T. Smith–Oliver et al., "Elevated Levels of TNF in the Joints of . . . ", Cytokine, 5(4):298–304 (1993).
T. Zielinski et al., "Effects of Leflunomide (HWA 486) on Expression . . . ", Agent Actions, 38 (1993).
T. Mattar et al., "Inhibition of the Epidermal Growth Factor Receptor . . . ", Fed. of European Biochemical Soc. 334(2):161–164 (1993).

Bartlett et al., "Leflunomide (HWA 486), A Novel Immunomodulating Compound For The Treatment Of Autoimmune Disorders And Reactions Leading to Transplantation Rejection", Agents and Actions, 32:10–21 (1991).
Axton et al., "Novel Immunosuppressive Butenamides", J. Chem. Soc. Perkin Trans., 1:2203–2213 (1992).
Vilcek et al., "Tumor Necrosis Factor", J. Biol. Chem., 266(12):7313–7316 (1991).
Bevilacqua et al., "Endothelial Leukocyte Adhesion Molecule 1: An Inducible Receptor For Neutrophils Related to Complement Regulatory Proteins And Lectins", Science 243:1160–1164 (1989).
Tracey et al., "Shock And Tissue Injury Induced By Recombinant Human Cachectin", Science, 234:470–474 (1986).
Waage et al., "Association Between Tumour Necrosis Factor In Serum And Fatal Outcome In Patients With Meningococcal Disease", Lancet 1:355–357 (1987).
Lahdevirta et al., "Elevated Levels of Circulating Cachectin/Tumor Necrosis Factor in Patients With Acquired Immunodeficiency Syndrome", Am. J. Med., 85:289–291 (1988).
Balkwill et al., "Evidence For Tumour Necrosis Factor/Cachetin Production In Cancer", Lancet 2:1229–1232 (1987).
Blanchard et al., "The Induction Of Tumour Necrosis Factor (TNF) In Murine Lung Tissue During Infection with *Legionella Pneumophila*: A Potential Protective Role", Lymphokine Res. 6:1421 (1987).
Erroi et al., "The Pneumotoxicant Paraquat Potentiates IL–1 and TNF Production By Human Mononuclear Cells", Agents Actions, 36:66–69 (1992).
Mustafa et al., "Correlation Of Interleukin–1β And Cachectin Concentrations In Cerebrospinal Fluid And Outcome From Bacterial Meningitis", J. Pediat., 115:208–213 (1989).
SCRIP, 1713:15 (1992).

*Primary Examiner*—Jerome D. Goldberg
*Attorney, Agent, or Firm*—Finnegan, Henderson, Farabow, Garrett & Dunner, L.L.P.

[57] ABSTRACT

N-(4-Trifluoromethylphenyl)-5-methylisoxazole-4-carboxamide is an effective compound for preventing and treating disorders in which tumor necrosis factor alpha is involved. It is used as a pharmaceutical.

1 Claim, No Drawings

USE OF LEFLUNOMIDE FOR INHIBITING TUMOR NECROSIS FACTOR ALPHA

This application is a continuation of application Ser. No. 08/177,981, filed Jan. 6, 1994, now abandoned.

Leflunomide (see formula, N- (4-trifluoromethylphenyl)-5-methylisoxazole-4-carboxamide) is already known as a chemical compound (EP 0013376, EP 0217206, U.S. Pat. No. 4,351,841, U.S. Pat. No. 4,965,276).

In addition to its antiinflammatory effects, which have already been disclosed, this substance also brings about immunomodulatory effects which qualify it for use in the treatment of autoimmune diseases and transplant rejection reactions. It is also already known that a metabolite with the designation N-(4-trifluoromethylphenyl)-2-cyano-3-hydroxycrotonamide (see formula) is responsible for the therapeutic effects of leflunomide.

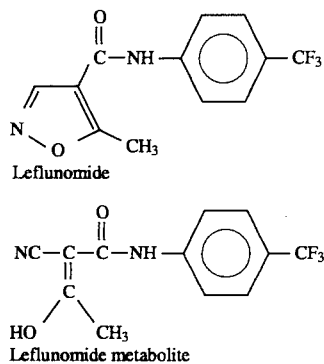

In correspondence with this finding, the pharmacological effects of leflunomide cited above can also be obtained by administering this said metabolite (Bartlett et al., Agents and Actions, 32 (1991) 10–21).

Axton et al., J. Chem. Soc. Perkin Trans. I (1992) 2203 ff. also describe how leflunomide does not represent the active principle and that, instead, this primary metabolite exhibits the biological effects.

It has been possible to demonstrate both in the literature (Bartlett et al., Agents and Actions, 32 (1991) 10–21) and in our own experiments that the therapeutic effects described in more detail below cannot be obtained by administering the leflunomide metabolite. Thus, it was found, in accordance with the invention, that leflunomide exerts a strong inhibitory effect on the synthesis and liberation of cytokines from human blood cells, whereas the leflunomide metabolite does not exhibit this advantageous effect.

Under the experimental conditions employed in accordance with the invention, no appreciable metabolism of leflunomide takes place, and the inhibitory effect is to be ascribed exclusively to the substance leflunomide.

The cytokines are a class of diverse, biologically highly potent, peptides whose structures are already known. It is likewise already known that they are induced and synthesized endogenously as transmitter substances.

The suppression of cytokines in the human or animal body is of great medical importance since excessive levels of these cytokines can lead to the occurrence or outbreak of numerous disorders.

Such disorders could be treated with a medicament which inhibits the undesirable effect of the cytokine, which might already be present, on the organ, cell, tissue and receptor systems of the body; however, it is now a further, significant advantage of the present invention that the use of leflunomide inhibits the actual synthesis and liberation of the cytokine so that the latter never even comes into being and the emergence of the disorder can thus be prevented at a very early phase.

The present invention relates to the use of leflunomide for preparing a pharmaceutical for preventing and treating disorders of the human and animal body in which the cytokine with the designation tumor necrosis factor alpha (TNFalpha) is involved.

The present invention further relates to the use of leflunomide for treating such disorders. The invention also relates to pharmaceuticals which contain an effective quantity of leflunomide in addition to pharmaceutically suitable and physiologically tolerated excipients, diluents and/or other active compounds and auxiliary substances.

The invention also relates to a process for preparing a pharmaceutical for preventing and treating disorders in which tumor necrosis factor alpha is involved, wherein leflunomide is brought into a suitable preparation form together with pharmaceutically suitable and physiologically acceptable excipients and, where appropriate, further suitable active compounds, additives or auxiliary substances.

TNFalpha and its disease-causing effects are described in detail in Ibelgaufts, Lexikon Zytokine (Cytokine Dictionary), Medikon Verlag, Munich 1992, and in the literature cited therein.

It can also be inferred from WO 92/02822, for example, that this cytokine possesses a broad spectrum of biological activity.

TNFalpha was originally named in accordance with its first effect to be recognized, namely its anti-tumor effect. Since then, the broad pleiotropic activities of TNFalpha have also been described (review in Vilcek and Lee, J. Biol. Chem. 266 (1991) 7313 ff.). TNFalpha can be synthesized in numerous cells, and many cells likewise possess specific receptors for this cytokine by way of which growth and transcription factors, acute phase proteins, and cell adhesion molecules such as ELAM-1 and ICAM-1 (Bevilacqa et al., Science 243 (1989) 1160), can in turn be induced.

TNFalpha possesses a potent effect in endotoxic shock (Tracey et al., Science 234 (1986) 470–474) and in cachexia (Oliff et al., Cell, 50 (1987) 555–563). TNFalpha likewise governs the fatal course of the disease in the case of malaria, meningitis (Waage et al., Lancet 1 (1987) 355–357), pneumonia (Blanchard et al., Lymphokine Res 6 (1987) 1421), and AIDS (Lahdevirta et al., Am. J. Med. 86 (1988) 289–291), as well as in cancer patients (Balkwill et al., Lancet 2 (1987) 1229–1232).

It is evident, therefore, that TNFalpha, in particular, occupies a central position as the trigger for various disorders and symptoms of disorders. These disorders are predominantly serious disorders which can currently either not be treated at all or only treated inadequately. For this reason too, the effect of leflunomide which has been discovered is of great importance.

The present invention furthermore relates to the use of leflunomide for preventing and treating disorders such as septic shock, cachexia, malaria, meningitis, pneumonia, AIDS, poisoning by endotoxins, connective tissue swellings, pulmonary intoxications, pulmonary edemas or chronic leukemia (Tracey et al., Science, 234 (1986) pages 314 ff.; Erroi et al., Agents Actions, 36 (1992) pages 66 ff.; Scrip, 1713, page 15 (1992); Mustafa et al., J. Pediat., 115 (1989) pages 1274 ff.).

Pharmaceutical forms and pharmaceutical preparations of leflunomide, which have been prepared in the customary manner, can also, in particular, be used for treating these disorders.

Suitable solid or liquid pharmaceutical preparation forms are, for example, granules, powders, coated tablets, tablets, (micro)capsules, suppositories, syrups, juices, suspensions, emulsions, drops or injectable solutions, as well as preparations having a protracted release of active compound, in whose preparation customary adjuvants, such as excipients, disintegrants, binding agents, coating agents, swelling agents, glidants, lubricants, flavorants, sweeteners or solubilizers are used. Frequently used auxiliary substances which may be mentioned are, for example, magnesium carbonate, titanium dioxide, lactose, mannitol and other sugars, talc, milk protein, gelatin, starch, cellulose and its derivatives, animal and plant oils, polyethylene glycols, and solvents, such as, for example, sterile water and monohydric or polyhydric alcohols, e.g. glycerol.

In human medicine, dose units of 3 to 5 mg, preferably 10, 25 or 50 mg, per patient (70 kg body weight) are administered. If required medically, the dose unit can be increased to 100, 200 or 500 mg per patient. Dosing can take place once daily to once weekly, preferably up to three or four times daily. Administration can be effected orally, peritoneally, intravenously, intraarticularly or transdermally in a customary manner. The corresponding doses to be administered within veterinary medicine can also be readily calculated from these data.

Finally, in the preparation of the abovementioned pharmaceutical preparation forms, leflunomide can also be formulated together with other suitable active compounds, for example antiuricopathic agents, blood platelet-aggregation inhibitors, analgesics, and other steroidal or non-steroidal antiinflammatory agents.

It was possible to demonstrate the effects of leflunomide experimentally on an isolated blood cell fraction (mononuclear cells), which cell fraction did not, to any appreciable extent, metabolize the leflunomide to its metabolites.

Example 1

The mononuclear cells from freshly isolated human citrate blood were enriched in accordance with known standard procedures (see Tiku et al., J. Immunol. 136/10 (1986) 3677): 10 ml of freshly prepared human citrate blood were carefully underlaid with 15 ml of Lymphoprep® (Molter GmbH, Heidelberg) and then centrifuged at 400 xg for 40 min. at 20° C. The cell fraction which was visible as a white ring at the phase boundary was removed with the aid of a syringe, diluted 1:1 (v/v) with PM-16 buffer (from Serva Feinbiochemica GmbH & Co. KG, Heidelberg) and then centrifuged once again, as above, for 10 min. The supernatant was washed with 10 ml of RPMI 1640 buffer (Gibco, Berlin) to which 300 mg/l L-glutamine had previously been added. The washed cell fraction was taken up in 1 ml of RPMI 1640 to which 300 mg/l L-glutamine, 25 mmol/l HEPES (Gibco, Berlin), 0.1 g/ml streptomycin and 0.1 g/ml penicillin had previously been added. Using a cell counter (type IT, from Coulter Diagnostics, Krefeld), the cell suspension, which is composed of about 90% lymphocytes and 10% monocytes, was adjusted to about 5 million cells/ml. Cell viability was monitored before and after the inhibition experiments using the known lactate dehydrogenase method. In this case, no change in viability was observed.

The synthesis and liberation of cellular TNFalpha was induced by adding a solution of 500 ng of lipopolysaccharide (Salmonella abortus equi, Sigma GmbH, Deisenhofen) in 0.01 ml of dimethyl sulfoxide/water (1:10, v/v) to 0.48 ml of the above-described cell fraction. At the same time, a solution of leflunomide or leflunomide metabolite in 0.01 ml of dimethylsulfoxide (for the final concentration in each case, see Tab. 1) was added to the cell fraction and the mixture was left at 37° C. for 20 h in a commercially available incubator. After cooling down to 0° C., the samples were centrifuged for 1 min. in a bench centrifuge. and in each case 0.025 ml aliquots of the supernatant were examined for their TNFalpha content using a "sandwich" enzyme immuno test kit (from Biermann GmbH, Bad Nauheim) in accordance with the manufacturer's instructions. The control values were determined without the addition of leflunomide or its metabolites and set at 100%. In particular, any possible influence of dimethylsulfoxide on the TNFalpha level was excluded by appropriate comparative measurements.

In addition, aliquots of the test sample containing leflunomide were removed in a time-dependent manner and tested for their content of leflunomide or leflunomide metabolite using high pressure liquid chromatography (C-18 column 3.9×150 mm, Waters GmbH, Eschborn, eluent: 600 ml of methanol/350 ml of water/50 ml of tetrahydrofuran/1 ml of phosphoric acid; flow rate 0.7 ml/min. at 2000 pounds per square inch (psi); detection in the ultraviolet range at 273 nm). It was found that, under the conditions employed, leflunomide is only very slowly, with a half life of about 10 hours, metabolized to its metabolites.

TABLE 1

| Substance under examination | Concentration in experiments mmol/l | TNFalpha in the supernatant % +/− standard deviation | Number n = |
| --- | --- | --- | --- |
| Leflunomide metabolite | 0.1 | 105 | 2 |
|  | 0.01 | 102 +/− 12 | 3 |
| Leflunomide | 0.1 | 28 +/− 5 | 3 |
|  | 0.05 | 35 | 2 |
|  | 0.01 | 100 +/− 15 | 5 |
| Without either | 0 | 100 |  |

The experiments in Tab. 1 demonstrate that the leflunomide metabolite has practically no effect on the TNFalpha level, whereas the TNFalpha level is clearly lowered following the addition of leflunomide.

Example 2

Preparation of N-(4-trifluoromethylphenyl)-5-methylisoxazole-4-carboxamide

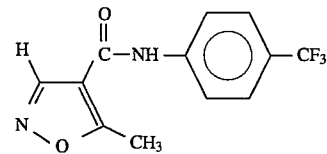

A solution of 0.05 mol of 4-methylisoxazole-4-carbonyl chloride (7.3 g) in 20 ml of acetonitrile is added dropwise, at room temperature, to a solution of 0.1 mol of 4-trifluoromethylaniline (16.1 g) in 150 ml of acetonitrile. After stirring for 20 minutes, the precipitated 4-trifluoromethylaniline hydrochloride is filtered off with suction and washed twice with 20 ml of acetonitrile on each occasion, and the combined filtrates are concentrated under reduced pressure. Yield: 12.8 g of white, crystalline N-(4-trifluoromethylphenyl)-5-methylisoxazole-4-carboxamide (leflunomide).

Example 3

Acute toxicity following intraperitoneal administration

The acute toxicity following intraperitoneal administration of the test substance was carried out using NMRI mice (20 to 25 g) and SD rats (120 to 195 g). The test substance was suspended in a 1% strength solution of sodium carboxymethyl cellulose. The different doses of the test substance were administered to the mice in a volume of 10 ml/kg of body weight and to the rats in a volume of 5 ml/kg of body weight. 10 animals were used per dose. After 3 weeks, the acute toxicity was determined by the method of Litchfield and Wilcoxon. The results are summarized in the table.

TABLE

|  | Leflunomide acute toxicity intra- peritoneally $LD_{50}$ (mg/kg) |
| --- | --- |
| NMRI mouse | 185 (163–210) |
| SD rat | 170 (153–189) |

We claim:

1. A method for the treatment of a condition characterized by an elevated tumor necrosis factor alpha level in a human or animal suffering from endotoxic shock, cachexia, malaria, meningitis, pneumonia, poisoning by endotoxins, connective tissue swellings, pulmonary intoxications or pulmonary edema, wherein the method comprises administering to said human or animal N-(4-trifluoromethylphenyl)-5-methyl-isoxazole-4-carboxamide in an amount sufficient to inhibit the synthesis and liberation of said tumor necrosis factor.

* * * * *